(12) United States Patent
Tagomori

(10) Patent No.: US 11,344,455 B2
(45) Date of Patent: May 31, 2022

(54) ABSORBENT ARTICLE

(71) Applicant: DAIO PAPER CORPORATION, Ehime (JP)

(72) Inventor: Junta Tagomori, Tochigi (JP)

(73) Assignee: DAIO PAPER CORPORATION, Ehime (JP)

(*) Notice: Subject to any disclaimer, the term of this patent is extended or adjusted under 35 U.S.C. 154(b) by 413 days.

(21) Appl. No.: 16/463,614

(22) PCT Filed: Nov. 27, 2017

(86) PCT No.: PCT/JP2017/042346
§ 371 (c)(1),
(2) Date: May 23, 2019

(87) PCT Pub. No.: WO2018/101191
PCT Pub. Date: Jun. 7, 2018

(65) Prior Publication Data
US 2020/0179187 A1   Jun. 11, 2020

(30) Foreign Application Priority Data

Nov. 29, 2016   (JP) .............................. JP2016-231448

(51) Int. Cl.
*A61F 13/537* (2006.01)
*A61F 13/53* (2006.01)
*A61F 13/532* (2006.01)

(52) U.S. Cl.
CPC ........ *A61F 13/53752* (2013.01); *A61F 13/53* (2013.01); *A61F 13/5323* (2013.01);
(Continued)

(58) Field of Classification Search
CPC ...... A61F 2013/53051; A61F 13/53752; A61F 13/53; A61F 13/5323; A61F 2013/530007; A61F 2013/530386; A61F 2013/530481
See application file for complete search history.

(56) References Cited

U.S. PATENT DOCUMENTS 4,333,463 A * 6/1982 Holtman ............... A61F 13/535
604/371
7,429,689 B2 * 9/2008 Chen ................... A61F 13/4751
428/131
(Continued)

FOREIGN PATENT DOCUMENTS

| JP | 2006-6741 | 1/2006 |
|---|---|---|
| JP | 2006-110329 | 4/2006 |

(Continued)

OTHER PUBLICATIONS

International Search Report dated Feb. 13, 2018 in International (PCT) Application No. PCT/JP2017/042346.

*Primary Examiner* — Susan S Su

(74) *Attorney, Agent, or Firm* — Wenderoth, Lind & Ponack, L.L.P.

(57) ABSTRACT

An absorbent article comprising a polymer sheet 4 in which a super absorbent polymer 12 exists between an upper layer sheet 10 arranged on the skin side and a lower layer sheet 11 arranged on the non-skin side is included. A fiber absorber 5 including pulp fiber is disposed adjacent to the surface on the skin side of an area corresponding to a body fluid discharge region H of a wearer in the polymer sheet 4. The super absorbent polymer 12 is not arranged in an area which overlaps with the fiber absorber 5, and is arranged in the other area. The water absorption rate of the absorbent article is not reduced even when water is repeatedly absorbed. Additionally, leakage is prevented, a wearing feeling is not worsened, and the adsorbent article may have a reduction in thickness.

6 Claims, 13 Drawing Sheets

(52) U.S. Cl.
CPC ............ *A61F 2013/530007* (2013.01); *A61F 2013/53051* (2013.01); *A61F 2013/530386* (2013.01); *A61F 2013/530481* (2013.01)

(56) References Cited

U.S. PATENT DOCUMENTS

| | | | | |
|---|---|---|---|---|
| 8,952,212 | B2* | 2/2015 | Bissah | A61F 13/513 |
| | | | | 604/378 |
| 2009/0112175 | A1* | 4/2009 | Bissah | A61F 13/4756 |
| | | | | 604/385.101 |
| 2011/0144604 | A1* | 6/2011 | Noda | A61F 13/475 |
| | | | | 604/361 |
| 2016/0175169 | A1 | 6/2016 | Bianchi et al. | |

FOREIGN PATENT DOCUMENTS

| | | | | |
|---|---|---|---|---|
| JP | 2008-237382 | | 10/2008 | |
| JP | 2012-152472 | | 8/2012 | |
| JP | 5175147 | | 4/2013 | |
| JP | 5318747 | | 10/2013 | |
| JP | 2014-113273 | | 6/2014 | |
| JP | 2014113273 | A * | 6/2014 | |
| JP | 2015-536230 | | 12/2015 | |
| JP | 2016-168300 | | 9/2016 | |
| WO | WO-0124756 | A1 * | 4/2001 | ......... A61F 13/4704 |

* cited by examiner

[Fig. 1]
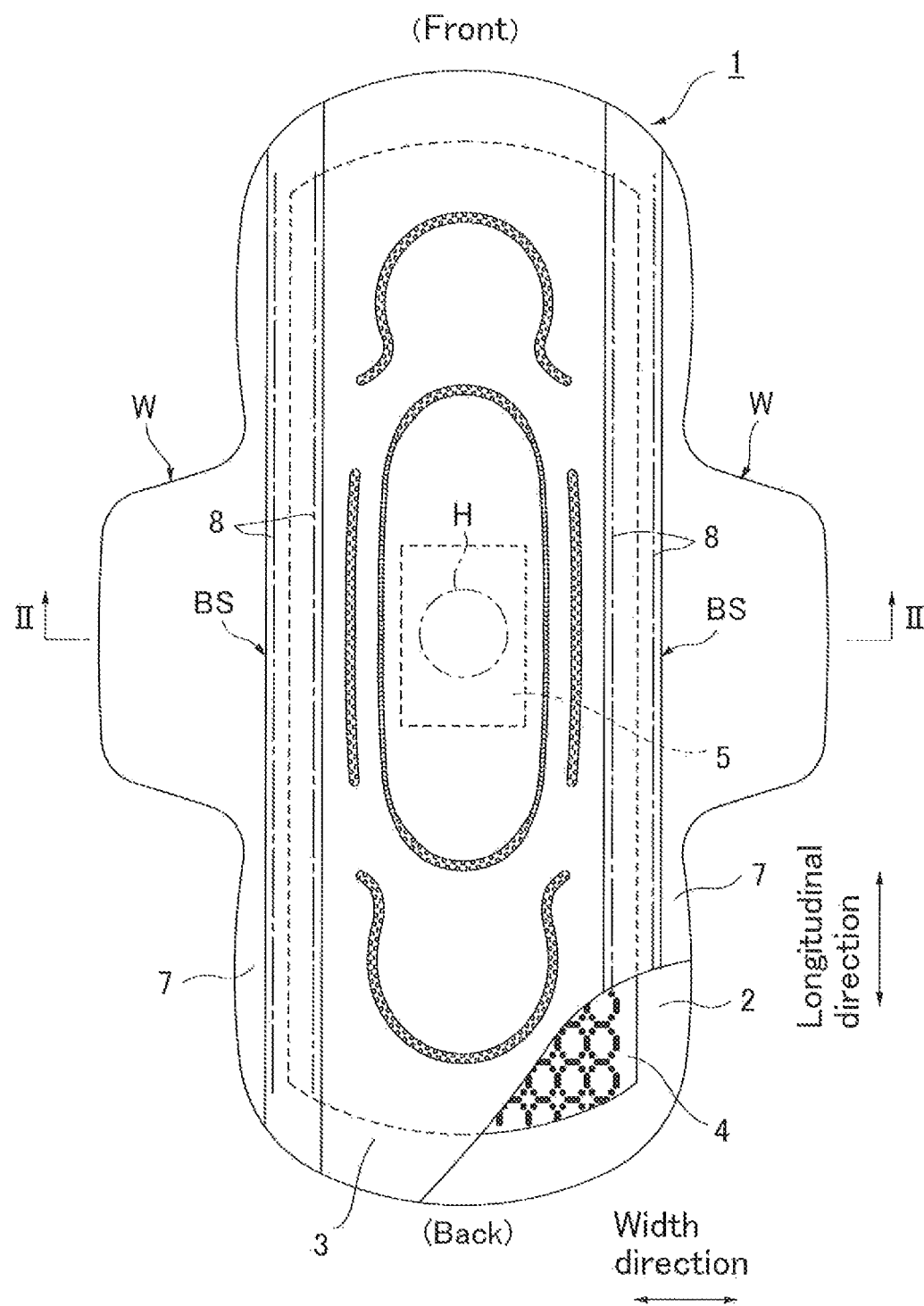

[Fig. 2]
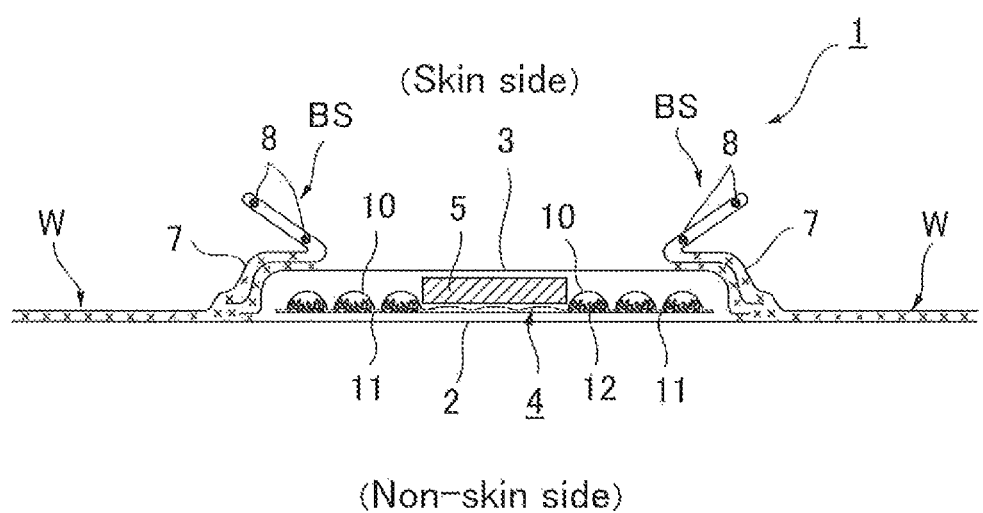

[Fig. 3]
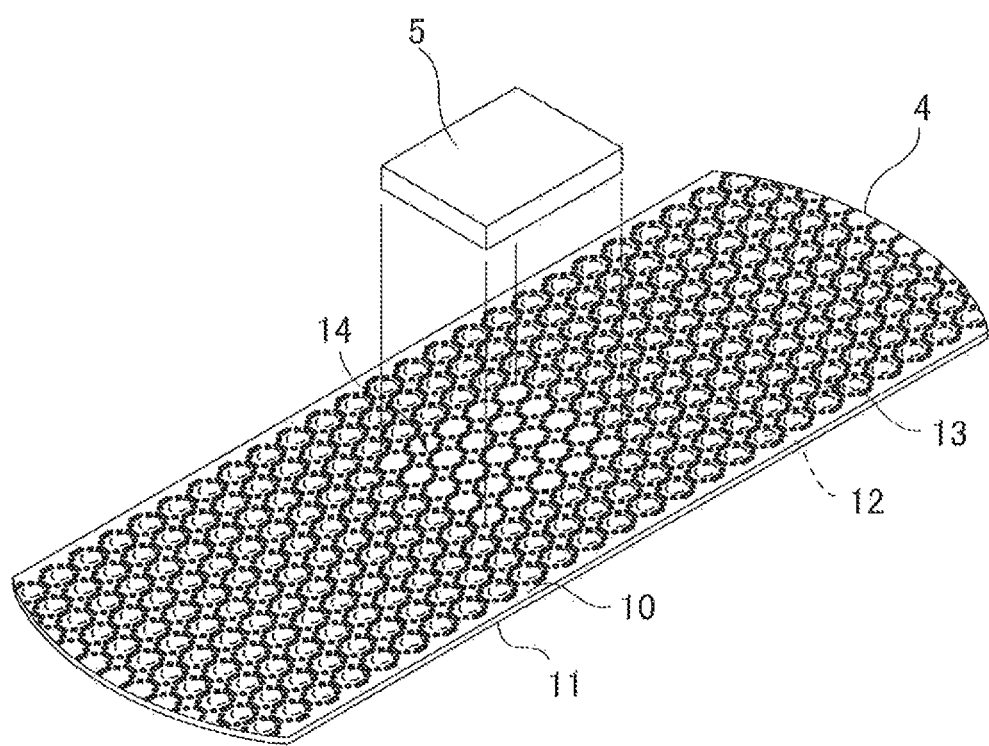

[Fig. 4]
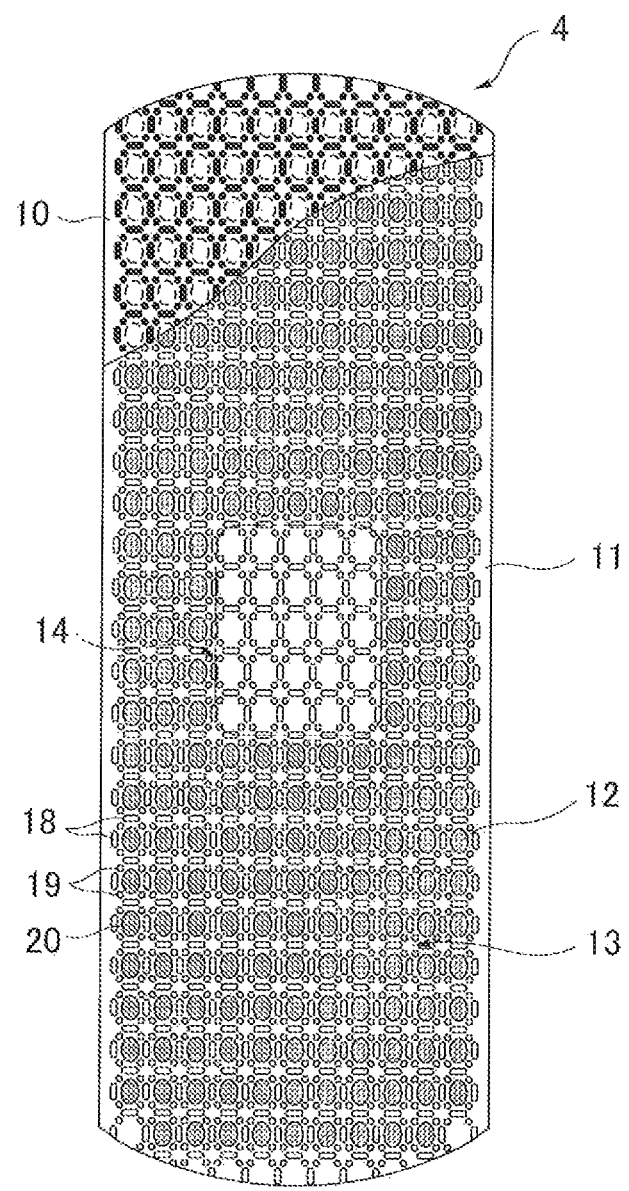

[Fig. 5]
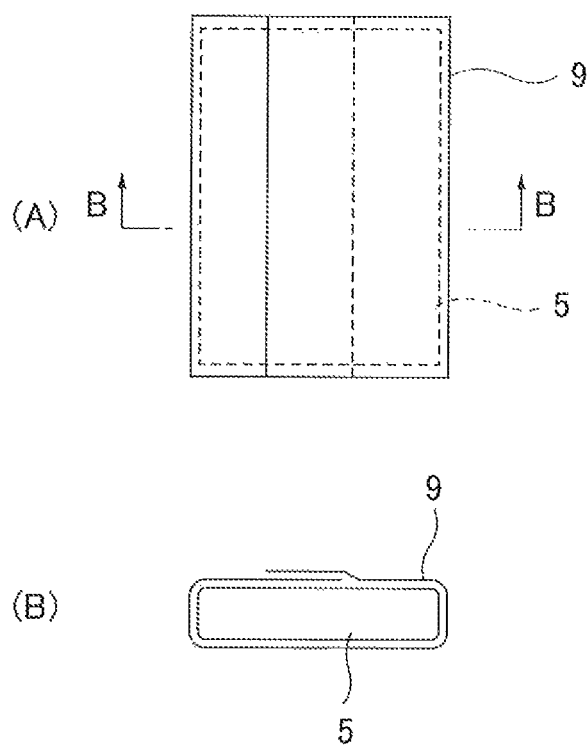

[Fig. 6]
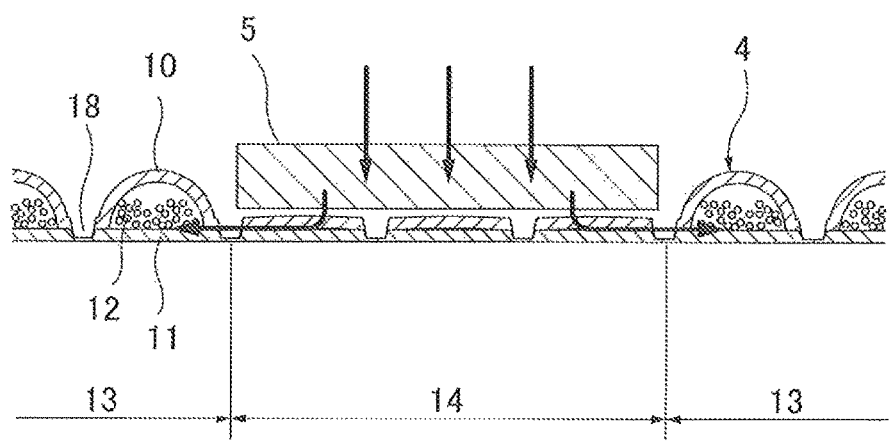

[Fig. 7]
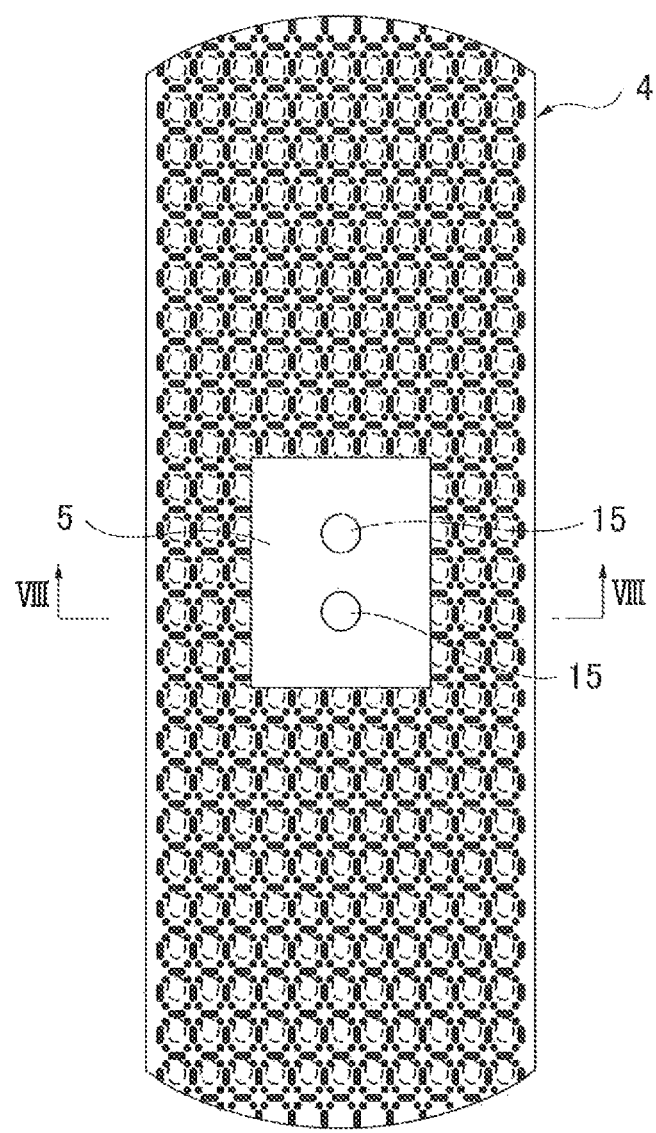

[Fig. 8]
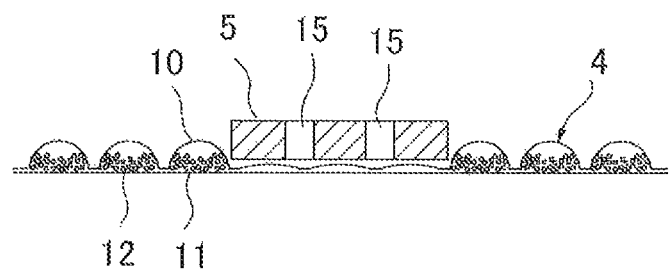

[Fig. 9]
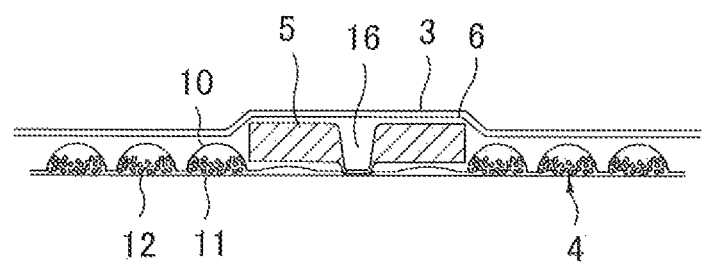
[Fig. 10]
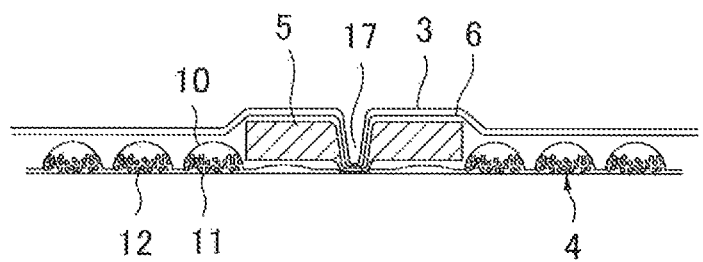

[Fig. 11]
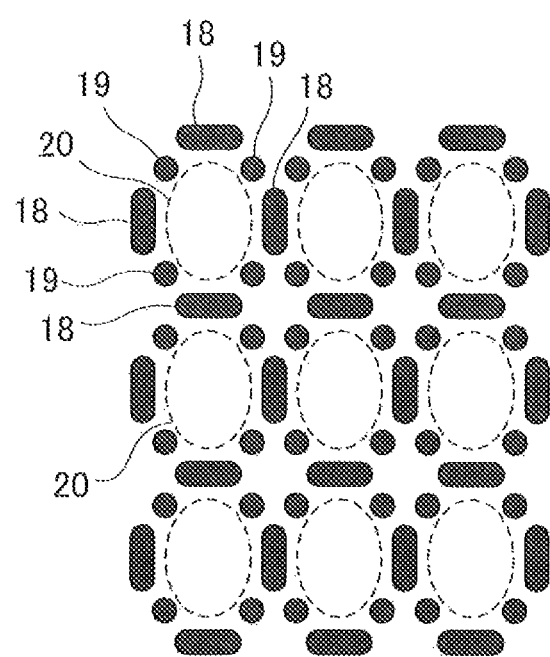

[Fig. 12]
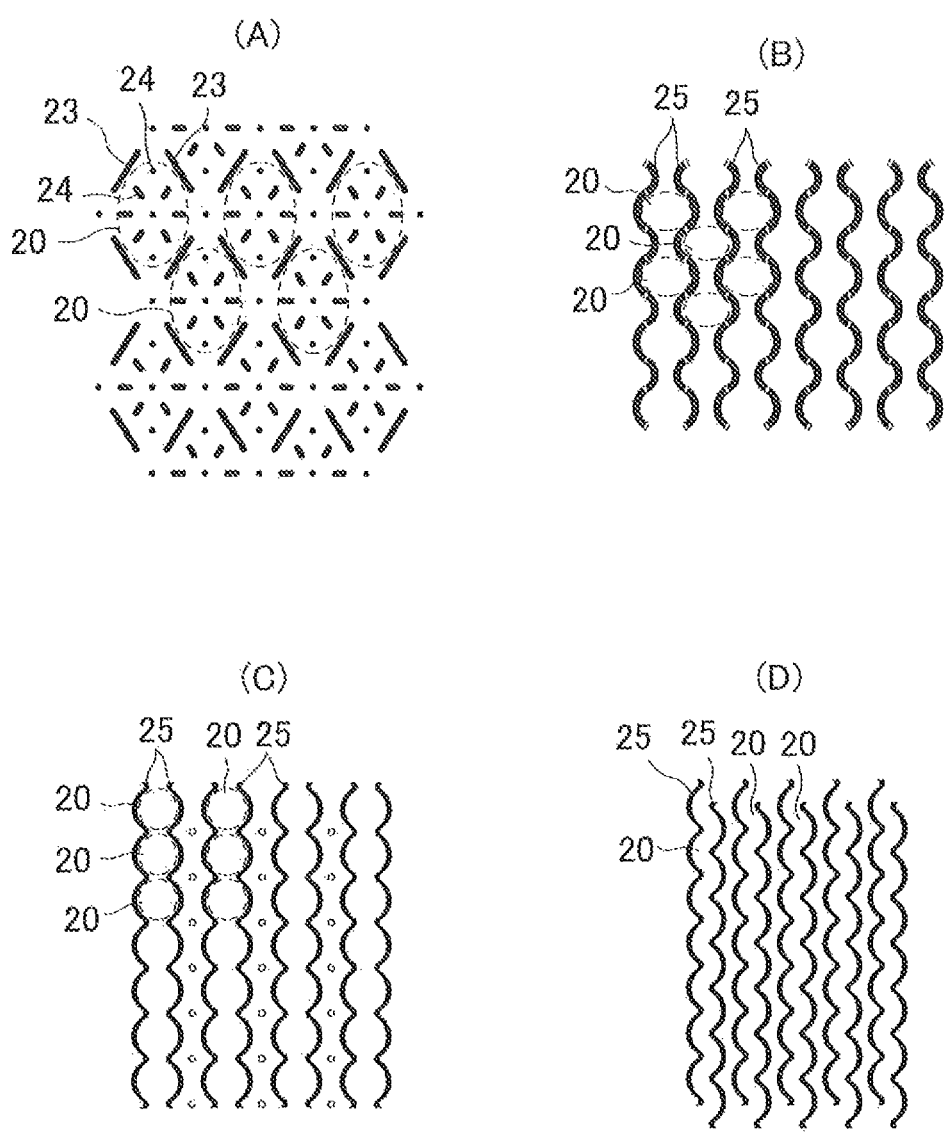

[Fig. 13]
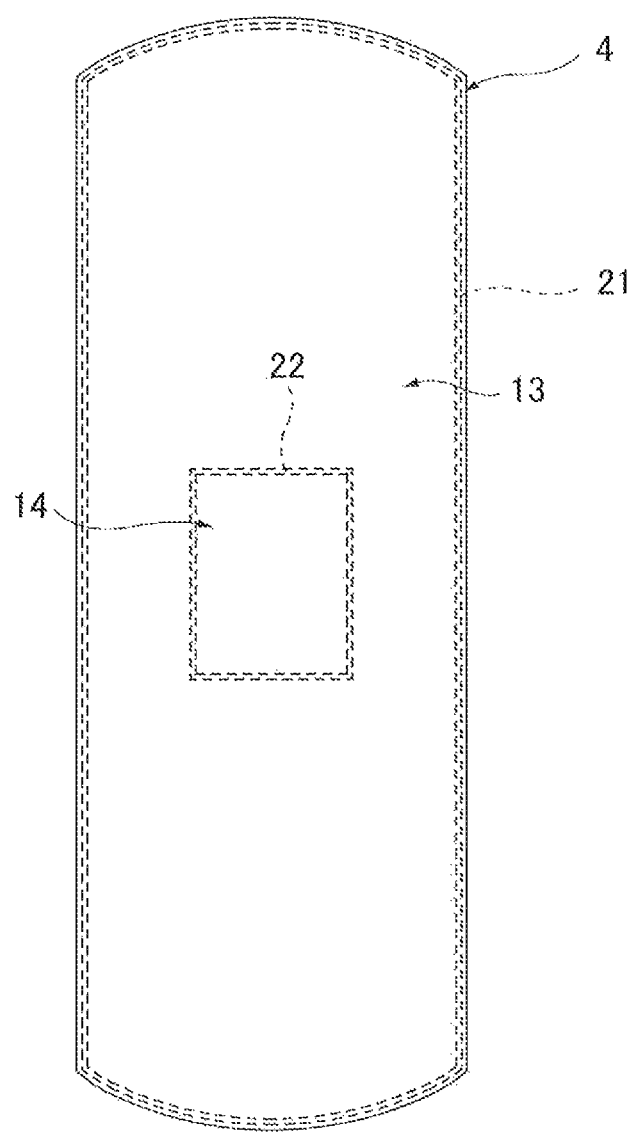

[Fig. 14]
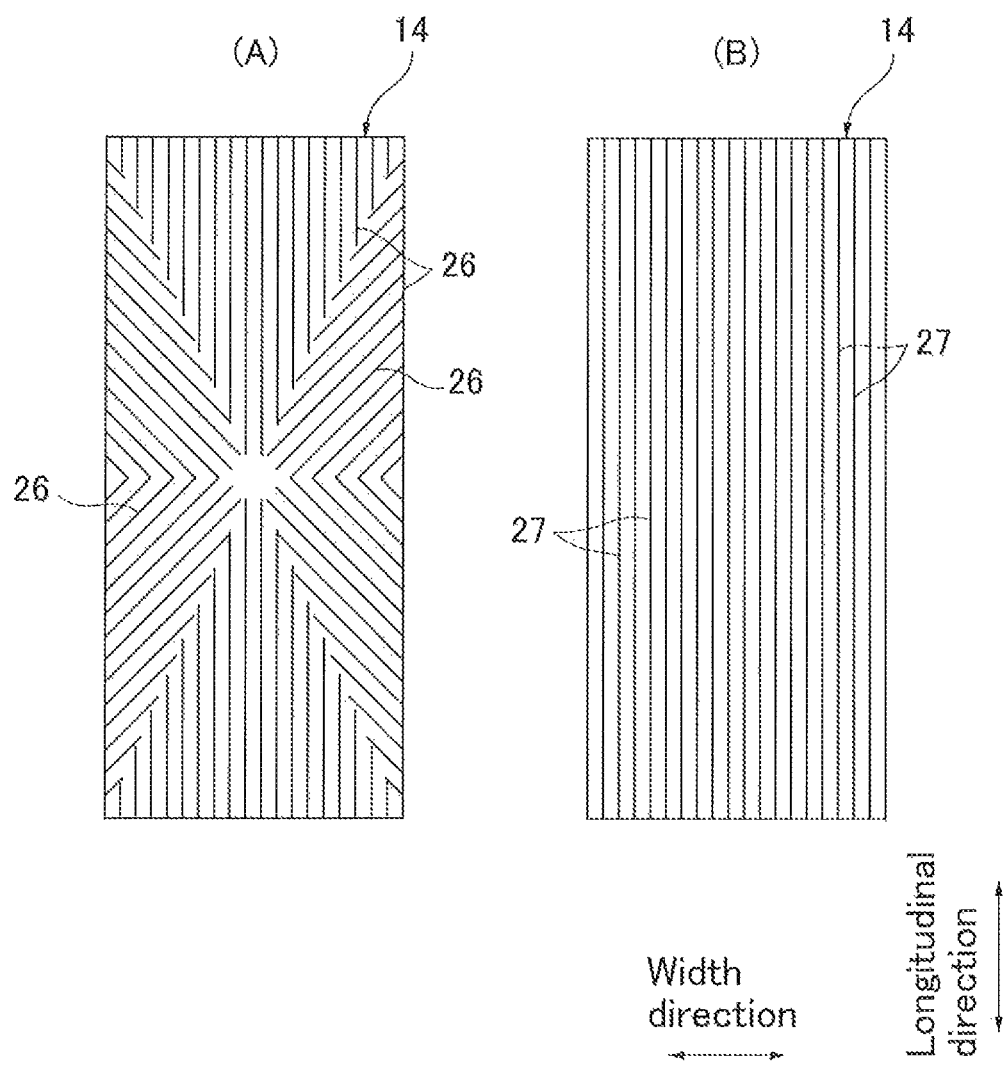

ABSORBENT ARTICLE

TECHNICAL FIELD

The present invention relates to an absorbent article such as a sanitary napkin, a pantiliner or an incontinence pad, and particularly an absorbent article including a polymer sheet in which a super absorbent polymer is arranged between an upper layer sheet and a lower layer sheet.

BACKGROUND ART

As the above absorbent article, those in which an absorber which functions to absorb and retain body fluids exists between an impermeable back-surface sheet such as a polyethylene sheet or a polyethylene sheet laminated nonwoven fabric, and a permeable front-surface sheet such as a nonwoven fabric or a permeable plastic sheet, have been conventionally known.

A large number of improvements have been made to this type of absorbent article, and as the above absorber one having a polymer sheet in which a super absorbent polymer (SAP) is arranged between two sheets (also referred to as SAP sheet, pulpless absorber, etc.) has been proposed. When the above polymer sheet is adopted as an absorber, because a reduction in thickness of an absorbent article is attempted and also a large amount of body fluid can be absorbed and retained, an excellent absorbent article is obtained. However, because aggregates of the super absorbent polymer in the form of granule are included in the inner part thereof, a body fluid is not easily infiltrated into the inner part of the polymer aggregates and flows around the surface of the above polymer aggregates, and what is called "gel blocking" in which the super absorbent polymer around this surface is bound to each other, easily occurs, and there has been a problem in that a desired water absorption power cannot be expressed.

As such absorbent article using a polymer sheet, Patent Literature 1 described below for example discloses an absorbent article, in which an absorbing structure includes an upper layer absorptive portion and a lower layer absorptive portion, the above upper layer absorptive portion is configured to include fluff pulp, a groove portion extending in the longitudinal direction of the absorbent article is formed on the skin-contact surface of the upper layer absorptive portion, the above lower layer absorptive portion is configured to include two sheet materials facing each other and a water-absorbent resin existing between both the sheet materials, and also both the sheet materials have a plurality of joint portions formed by joining the sheet materials each other without the water-absorbent resin, the above plurality of joint portions extend in the longitudinal direction and also are arranged in parallel at predetermined intervals in the width direction, the above groove portion and joint portions overlap in a planar view in an inside leg portion located in the inside leg of a wearer when wearing, and the surface sheet, upper layer absorptive portion and lower layer absorptive portion are consolidated in the above groove portion.

In addition, Patent Literature 2 described below discloses an absorbent article, which has, from the top sheet side, an upper sheet absorption layer, a fiber assembled layer, and a lower sheet absorption layer in this order. The above upper sheet absorption layer and the above lower sheet absorption layer each have a water-absorbent resin and do not have pulp fiber between nonwoven fabric sheets, and have a plurality of the existence areas of water-absorbent resin, in which a water-absorbent resin is arranged, and the non-existence areas of water-absorbent resin adjacent to the above existence areas of water-absorbent resin between the above nonwoven fabric sheets. The nonwoven fabric sheets are joined each other to form a sealed portion in the above non-existence area of water-absorbent resin.

CITATION LIST

Patent Literature

Patent Literature 1: Japanese Patent No. 5175147
Patent Literature 2: Japanese Patent No. 5318747

SUMMARY OF INVENTION

Technical Problem

In the absorbent articles described in Patent Literatures 1 and 2 described above, a pulp fiber stacked absorber layer functions as an area to temporarily stock a body fluid and an area to spread a body fluid by combining a polymer sheet and a pulp fiber stacked absorber, and the absorption rate and return amount are improved. However, the absorber is configured by laminating a polymer sheet and a pulp fiber stacked absorber, and thus a sufficient reduction in thickness has not been necessarily available.

In addition, in the absorbent article in Patent Literature 1 described above, a water-absorbent resin area in a lower layer absorptive portion (polymer sheet) exists on the lower layer side of an area which overlaps with an upper layer absorptive portion including fluff pulp (fiber absorber). Accordingly, the fluid moving rate from the upper layer absorptive portion to the lower layer absorptive portion, which has been swollen due to previous water absorption, is reduced when water is repeatedly absorbed, and there has been a case where an absorption rate which can be sufficiently satisfied is not obtained.

In the absorbent article described in Patent Literature 2 described above, furthermore, a polymer sheet is arranged on the uppermost layer of the absorbing structure, and particularly this polymer sheet is located on the uppermost layer also in a site corresponding to a body fluid discharge region of a wearer. Accordingly, the absorption rate is poor immediately after a body fluid discharge, and also a reduction in the absorption rate is significant when water is repeatedly absorbed, and there has been a possibility that leakage occurs due to the flow of fluid on the surface.

In conventional absorbent articles configured by laminating a polymer sheet and a fiber absorber, in a case where a middle-height portion is formed by the above fiber absorber in an area including a body fluid discharge region, when a super absorbent polymer is arranged in a portion with which the middle-height portion overlaps in the above polymer sheet in the same amount as in a portion other than the middle-height portion, the middle-height portion is also lifted toward the skin by the swollen super absorbent polymer when a fluid is absorbed. Accordingly, the middle-height portion bites into the body more than necessary, and a wearing feeling can be worsened.

Therefore, a main subject of the present invention is to provide an absorbent article wherein a reduction in thickness is certainly attempted, and also the water absorption rate is not reduced even when water is repeatedly absorbed, leakage is prevented, and a wearing feeling is not worsened.

Solution to Problem

In order to solve the above subject, there is provided as the present invention according to claim 1 an absorbent article, including a polymer sheet in which a super absorbent polymer exists between an upper layer sheet arranged on the skin side and a lower layer sheet arranged on the non-skin side, the absorbent article being characterized in that a fiber absorber including pulp fiber is disposed adjacent to the surface on the skin side of an area corresponding to a body fluid discharge region of a wearer in the polymer sheet, and the super absorbent polymer is not arranged in an area which overlaps with the fiber absorber, and is arranged in the other area.

In the invention according to claim 1 above, the fiber absorber including pulp fiber is disposed adjacent to the surface on the skin side of an area corresponding to a body fluid discharge region of a wearer in the above polymer sheet, and the above fiber absorber is not disposed in the other area. Accordingly a reduction in thickness of an absorbent article by using the above polymer sheet can be certainly attempted.

In addition, the absorbent article is characterized in that the super absorbent polymer in the above polymer sheet is not arranged in an area which overlaps with the above fiber absorber and is arranged in the other area. In such absorbent article, a body fluid discharged from a body fluid discharge region is absorbed by the fiber absorber and then penetrates into an area in which the super absorbent polymer is not arranged in the polymer sheet (non-polymer area), passes between the upper layer sheet and lower layer sheet of the polymer sheet, spreads into the surrounding area in which the super absorbent polymer is arranged (polymer arranged area), and is absorbed and retained in the super absorbent polymer. Therefore, when a body fluid moves from the fiber absorber to the polymer sheet, the body fluid penetrates between the upper layer sheet and lower layer sheet of the polymer sheet and into the upper layer sheet and the lower layer sheet and spreads into the polymer sheet in the surface direction, and simultaneously is absorbed in the super absorbent polymer in the polymer sheet. Accordingly, e.g. gel blocking does not occur and a significant reduction in the water absorption rate is not caused even when water is repeatedly absorbed, and leakage of the body fluid can be also prevented. In addition, in the above polymer sheet, the super absorbent polymer is not arranged in an area which overlaps with the fiber absorber, and thus in the area which overlaps with the fiber absorber in the above polymer sheet, a lift toward the skin due to swelling of the super absorbent polymer does not occur when a fluid is absorbed. Accordingly, a worsening of a wearing feeling due to the fiber absorber being lifted toward the skin and biting into the body more than necessary can be prevented.

There is provided as the present invention according to claim 2 the absorbent article according to claim 1, wherein the above fiber absorber includes only pulp fiber or includes pulp fiber and a super absorbent polymer.

In the prevention according to claim 2 above, the above fiber absorber may be configured from only pulp fiber so that a body fluid discharged from a body fluid discharge region can quickly move to the polymer sheet, or may include a super absorbent polymer so that the fiber absorber itself will have absorption ability.

There is provided as the present invention according to claim 3 the absorbent article according to claim 1 or 2, wherein the surface on the skin side of the above fiber absorber is located at a height almost equal to that of the surface on the skin side of an area in which the above super absorbent polymer is arranged in the above polymer sheet, or located closer to the skin.

In the invention according to claim 3 above, in a state in which the fiber absorber is disposed on the surface on the skin side of the polymer sheet, the surface on the skin side of the above fiber absorber is located at a height almost equal to that of the surface on the skin side of the surrounding area in which the super absorbent polymer is arranged, or located closer to the skin. When the surface on the skin side of the fiber absorber and the surface on the skin side of the surrounding polymer sheet are formed at an almost equal height, a reduction in thickness can be more certainly attempted. When the surface on the skin side of the fiber absorber is formed at a higher position toward the skin than the surface on the skin side of the surrounding polymer sheet, the above fiber absorber functions as a middle-height portion, and adhesion to a body fluid discharge region of a wearer can be improved.

There is provided as the present invention according to claim 4 the absorbent article according to any of claims 1 to 3, wherein one or more openings penetrating through the front and back surfaces are formed in the above fiber absorber.

In the prevention according to claim 4 above, one or more openings penetrating through the front and back surfaces are formed in the above fiber absorber, and thus a body fluid can quickly move from the fiber absorber to the polymer sheet through the openings.

There is provided as the present invention according to claim 5 the absorbent article according to any of claims 1 to 4, wherein a concave portion depressed to the above polymer sheet is formed on the surface on the skin side of the above fiber absorber.

In the invention according to claim 5 above, a concave portion depressed from the surface on the skin side of the fiber absorber to the polymer sheet is formed, and thus a body fluid having infiltrated into this concave portion can quickly move to the polymer sheet.

There is provided as the present invention according to claim 6 the absorbent article according to any of claims 1 to 5, wherein an area in which the above super absorbent polymer is arranged is divided into a plurality of defined areas by joint portions joining the above upper layer sheet and lower layer sheet and also the above super absorbent polymer is arranged in the above defined areas, or an area in which the above super absorbent polymer is arranged is not divided by joint portions joining the above upper layer sheet and lower layer sheet and the above super absorbent polymer is arranged on a whole surface in the above polymer sheet.

In the invention according to claim 6 above, as the arrangement form of the super absorbent polymer in an area in which the above super absorbent polymer is arranged, two forms are specified. As the first form, an area in which the above super absorbent polymer is arranged is divided into a plurality of defined areas by joint portions joining the above upper layer sheet and lower layer sheet, and also the super absorbent polymer is arranged in these defined areas. Because of this, the portion of a defined area in which the above super absorbent polymer is arranged is lifted when water is absorbed; however, the portions in which the joint portions are arranged around the defined area are not lifted. Accordingly, a fluid easily spreads using the relatively depressed joint portion as a channel even when water is repeatedly absorbed.

Next, as the second form, an area in which the super absorbent polymer is arranged is not divided by joint portions joining the upper layer sheet and lower layer sheet, and the super absorbent polymer is arranged on a whole surface.

Because of this, the flowability of the super absorbent polymer increases in the area in which the super absorbent polymer is arranged, and a reduction in absorption performance due to gel blocking does not easily occur.

Advantageous Effect of Invention

As described above in detail, according to the present invention, a reduction in thickness can be certainly attempted, and also a significant reduction in the water absorption rate is not caused even when water is repeatedly absorbed, leakage can be prevented, and also a wearing feeling is not worsened.

BRIEF DESCRIPTION OF DRAWING

FIG. 1 is a partially cutaway development view of a sanitary napkin 1 according to the present invention.

FIG. 2 is an arrow view taken along the line II-II in FIG. 1.

FIG. 3 is an exploded perspective view of a polymer sheet 4 and fiber absorber 5.

FIG. 4 is a partially cutaway development view of a polymer sheet 4.

FIG. 5(A) is a plan view which shows a fiber absorber 5, and FIG. 5(B) is an arrow view taken along the line B-B.

FIG. 6 is a cross-section view of a polymer sheet 4 and fiber absorber 5 which shows the flow of body fluid when water is absorbed.

FIG. 7 is a plan view of a polymer sheet 4 and fiber absorber 5 according to a modified example.

FIG. 8 is an arrow view taken along the line VIII-VIII in FIG. 7.

FIG. 9 is an enlarged cross-section view of an important part in a sanitary napkin 1 according to a modified example (part 1).

FIG. 10 is an enlarged cross-section view of an important part in a sanitary napkin 1 according to a modified example (part 2).

FIG. 11 is an enlarged plan view of joint portions 18 and 19.

FIGS. 12(A) to (D) are enlarged plan views of joint portions in a modified example.

FIG. 13 is a plan view of a polymer sheet 4 according to a modified example.

FIGS. 14(A) and (B) are plan views of a non-polymer area 14 in a polymer sheet 4.

DESCRIPTION OF EMBODIMENT

Embodiments of the present invention will now be described in detail with reference to drawings.

[Basic Configuration of Sanitary Napkin 1]

The sanitary napkin 1 according to the present invention is configured from an impermeable back-surface sheet 2 having e.g. a polyethylene sheet or a polypropylene sheet, a permeable front-surface sheet 3 through which e.g. menstrual blood and vaginal discharge quickly pass, a polymer sheet 4 in which a super absorbent polymer is arranged between two sheets existing between both the sheets 2 and 3, a fiber absorber 5 including pulp fiber disposed adjacent to the surface on the skin side of a predetermined position in the above polymer sheet 4, and, as needed, a second sheet 6 having e.g. a hydrophilic nonwoven fabric disposed adjacent to the non-skin side of the above permeable front-surface sheet 3, and side nonwoven fabrics 7, 7 disposed on each of both lateral portions on the front surface along the longitudinal direction as shown in FIG. 1 and FIG. 2. In addition, in the surroundings of the above polymer sheet 4, the outer edge portions of the above impermeable back-surface sheet 2 and the permeable front-surface sheet 3 are joined by an adhesive such as a hot melt adhesive or a bonding means such as heat sealing in the front and back end edge portions in the longitudinal direction of the napkin. In the edge portions on both sides, the above impermeable back-surface sheet 2 and the above side nonwoven fabric 7, which extends more laterally than the side edge of the polymer sheet 4, are joined by an adhesive such as a hot melt adhesive or a bonding means such as heat sealing. A peripheral flap portion in which the polymer sheet 4 does not exist is formed in the outer periphery.

The structure of the above sanitary napkin 1 will now be described in more detail.

A sheet material having at least water sealing properties, for example, an olefin-based resin sheet such as polyethylene or polypropylene is used for the above impermeable back-surface sheet 2. In addition to this, a laminated nonwoven fabric in which a nonwoven fabric is laminated on e.g. a polyethylene sheet, and moreover a nonwoven fabric sheet in which a waterproof film is allowed to exist to substantially secure impermeability (in this case, an impermeable back-surface sheet is configured from the waterproof film and nonwoven fabric), for example, can be used. In recent years there is a tendency to use one having moisture permeability from the viewpoint of preventing humidity. This water sealing and moisture permeable sheet material is a microporous sheet obtained by melting and kneading an inorganic filler in an olefin-based resin such as polyethylene or polypropylene to form a sheet and then drawing the sheet in the uniaxial or biaxial direction.

Next, a porous or nonporous nonwoven fabric or a porous plastic sheet, for example, is suitably used as the above permeable front-surface sheet 3. As a material fiber to make a nonwoven fabric, for example, a synthetic fiber such as an olefin-based fiber, e.g. polyethylene or polypropylene, a polyester-based fiber, or a polyamide-based fiber, and also a regenerated fiber such as rayon or cupra, and a natural fiber such as cotton can be used, and a nonwoven fabric obtained by a proper processing method such as a spunlace method, a spunbond method, a thermal bond method, a melt blown method, or a needle punch method can be used. Among these processing methods, a spunlace method and a spunbond method are excellent in terms of flexibility and rich drape properties respectively, and a thermal bond method and an air through method are excellent in terms of bulkiness and high compression restorability. The nonwoven fabric fiber can be either long fiber or short fiber, and short fiber is preferably used to provide a texture of towel cloth. In addition, an olefin-based fiber such as polyethylene or polypropylene with a relatively low melting point is preferably used to make emboss treatment easy. In addition, a core sheath fiber having a fiber with a high melting point as a core and a fiber with a low melting point as a sheath, a side-by-side fiber, and a conjugated fiber such as a segmented fiber can be also suitably used. It is not required that the above permeable front-surface sheet 3 be provided when the upper layer sheet 10 of the polymer sheet 4 described in detail in a later paragraph makes a skin-contact surface layer.

The above second sheet 6 is only needed to be hydrophilic to a body fluid. Specifically, a fiber in which a material itself has hydrophilicity by using a regenerated fiber such as rayon or cupra, or a natural fiber such as cotton is used, or a fiber to which hydrophilicity is provided by surface treatment of a synthetic fiber such as an olefin-based fiber e.g. polyethylene or polypropylene, a polyester-based fiber or a polyamide-based fiber using a hydrophilizing agent can be used. In addition, the above second sheet 6 may have a porous film layer on the back-surface side (non-skin side) for the purpose of providing body, and also a material including pulp may be used. The above second sheet 6 is formed with a size at least covering the whole of the above polymer sheet 4, and is preferably formed in almost the same shape as that of the above permeable front-surface sheet 3.

On the other hand, the side nonwoven fabrics 7, 7 along the longitudinal direction spreading over an almost whole length of the napkin 1 are provided on each of both lateral portions on the front surface side of the sanitary napkin 1. Wing-shaped flaps W, Ware formed by these side nonwoven fabrics 7, 7, part of which extends laterally, and part of the impermeable back-surface sheet 2, which similarly extends laterally.

As the above side nonwoven fabric 7, a water repellent nonwoven fabric or a hydrophilic nonwoven fabric can be used in terms of functions emphasized. For example, when a function of preventing e.g. menstrual blood and vaginal discharge from penetrating or a function of increasing a touch is emphasized, it is desired to use a water repellent nonwoven fabric on which e.g. a silicon-based, paraffin-based, or alkyl chromic chloride-based repellent is coated. In addition, when absorption properties in the above wing-shaped flaps W, W for e.g. menstrual blood are emphasized, it is desired to use a hydrophilic nonwoven fabric to which hydrophilicity is provided by applying capillarity after a synthetic fiber is made swollen or porous by e.g. a method in which polymerization is carried out in the coexistence of e.g. an oxidation product of a compound having a hydrophilic group, for example polyethylene glycol, in the production step of the synthetic fiber, or a method in which porosity is obtained by partially melting the front surface by treatment with a metallic salt such as tin chloride and a metal hydroxide is deposited thereon.

As shown in FIG. 2, on the inward side of the above side nonwoven fabric 7, one or more, two in an example shown, string-like elastic stretch members 8, 8 which fold the above side nonwoven fabric 7 almost in half, and in which both ends or proper positions in the longitudinal direction are fixed in an intermediate portion in the height direction, are disposed in the inner part of the double sheet, and 3-D gathers BS, BS are formed in which the above double sheet portion is lifted toward the skin by the contractive force.

[Polymer sheet 4 and fiber absorber 5]

The polymer sheet 4 which exists between the above impermeable back-surface sheet 2 and permeable front-surface sheet 3 has a structure in which the super absorbent polymer 12 is arranged between the upper layer sheet 10 arranged on the skin side (the side of the permeable front-surface sheet 3) and the lower layer sheet 11 arranged on the non-skin side (the side of the impermeable back-surface sheet 2). A fiber absorber such as pulp is not arranged and only the super absorbent polymer 12 in the form of granule is arranged between the above upper layer sheet 10 and the lower layer sheet 11. Because of this, the thickness of the above polymer sheet 4 can be made thinner, and a reduction in thickness can be certainly attempted.

As the above upper layer sheet 10 making the above polymer sheet 4, a porous or nonporous nonwoven fabric or a porous plastic sheet is used. As a material fiber making a nonwoven fabric, as with the case of the above permeable front-surface sheet 3, for example, a synthetic fiber such as an olefin-based fiber, e.g. polyethylene or polypropylene, a polyester-based fiber, or a polyamide-based fiber, and also a regenerated fiber such as rayon or cupra, or a natural fiber such as cotton can be used. The processing method for the above nonwoven fabric is not limited; however, a processing method by which the fiber density of a product obtained increases such as a spunbond method, a melt blown method, or a needle punch method is preferably used to prevent the falling of the super absorbent polymer 12. The opening diameter of the above porous plastic sheet is preferably smaller than the external form of the super absorbent polymer 12 to prevent the falling of the super absorbent polymer 12.

In addition, as the above lower layer sheet 11, a porous or nonporous nonwoven fabric or a porous plastic sheet, and also a sheet material having water sealing properties can be used. As with the case of the above upper layer sheet 10, the processing method for the nonwoven fabric is not limited; however, a processing method by which the fiber density of a product obtained increases such as a spunbond method, a melt blown method, or a needle punch method is preferably used to prevent the falling of the super absorbent polymer 12. The opening diameter of the above porous plastic sheet is preferably smaller than the external form of the super absorbent polymer 12 to prevent the falling of the super absorbent polymer 12. As the sheet material having the above water sealing properties, the same materials as for the above impermeable back-surface sheet 2 can be used.

Examples of the above super absorbent polymer 12 include crosslinked products of polyacrylic acid salts, self-crosslinked polyacrylic acid salts, saponified products of crosslinked products of acrylic acid ester-vinyl acetate copolymers, crosslinked products of isobutylene-maleic anhydride copolymers, crosslinked products of polysulfonic acid salts, partially crosslinked products of water swellable polymers such as polyethylene oxide and polyacrylamide, and the like. Among these, an acrylic acid or an acrylic acid salt-based polymer having an excellent water absorption amount and water absorption rate is suitable. In the production process of the super absorbent polymer having the above water absorption performance, the water absorption power and water absorption rate can be adjusted by adjusting the crosslink density and crosslink density gradient.

In the sanitary napkin 1, the fiber absorber 5 including pulp fiber is disposed adjacent to the surface on the skin side of an area corresponding to a body fluid discharge region H of a wearer in the above polymer sheet 4. The area corresponding to a body fluid discharge region H of a wearer is an area with which the body fluid discharge region H of a wearer comes into contact when wearing the sanitary napkin 1, and is a range in the longitudinal direction of the napkin almost equal to a range in which the above wing-shaped flap W is formed in an intermediate portion in the longitudinal direction of the sanitary napkin 1, and also is a central area in the width direction of the sanitary napkin 1.

As shown in FIG. 1, a concave groove depressed from the front-surface side of the permeable front-surface sheet 3 to the side of the impermeable back-surface sheet 2 may be formed to surround the surroundings of an area in which the above fiber absorber 5 is disposed.

The above super absorbent polymer 12 in the above polymer sheet 4 is not arranged in an area which overlaps with the above fiber absorber 5, and is arranged in the other area. That is, as shown in FIG. 3 and FIG. 4, the above polymer sheet 4 is configured from a polymer arranged area 13 in which the super absorbent polymer 12 exists between the above upper layer sheet 10 and lower layer sheet 11 in an area which does not overlap with the above fiber absorber 5, and a non-polymer area 14 in which the super absorbent polymer 12 does not exist between the above upper layer sheet 10 and lower layer sheet in an area which overlaps with the above fiber absorber 5.

The above polymer arranged area 13 is an area in which the above super absorbent polymer 12 is sealed at a predetermined weight between the above upper layer sheet 10 and lower layer sheet 11. The weight of the super absorbent polymer 12 in the above polymer arranged area 13 is on average 60 to 300 g/m², and preferably 110 to 150 g/m² in the above polymer arranged area 13.

The above non-polymer area 14 is an area in which the upper layer sheet 10 and the lower layer sheet 11 are laminated, and an area in which the super absorbent polymer 12 does not exist between these sheets 10 and 11 at all, or the super absorbent polymer 12 exists in a slight amount because, when scattering the super absorbent polymer 12 on the above polymer arranged area 13, the super absorbent polymer 12, for example, spills out, but the amount is extremely low compared to that of the above polymer arranged area 13.

The above non-polymer area 14 is formed with a size equal to or more than the planar shape of the above fiber absorber 5 in an area corresponding to a body fluid discharge region H of a wearer. The above non-polymer area 14 is an area in which just the upper layer sheet 10 and the lower layer sheet 11 are laminated, and thus a depressed area in which the surface on the skin side is slightly depressed compared to the surrounding polymer arranged area 13 is formed because the above super absorbent polymer 12 does not exist. In a state in which the above fiber absorber 5 is arranged on the skin side of the polymer sheet 4, the above fiber absorber 5 is arranged to fit the relatively depressed non-polymer area 14.

The above fiber absorber 5 includes, for example, only pulp fiber such as fluff pulp, or is configured from pulp fiber and a super absorbent polymer. The above super absorbent polymer is, for example, in the form of a granular powder, and dispersed and mixed in pulp making the absorber 4. Examples of the above pulp include those having a chemical pulp obtained from wood, a cellulose fiber such as a dissolving pulp, or an artificial cellulose fiber such as rayon or acetate, and a softwood pulp having a longer fiber length than a hardwood pulp is suitably used in terms of functions and costs. The weight of the above pulp is 40 to 400 g/m², and preferably 100 to 300 g/m². The weight of the super absorbent polymer in the above fiber absorber 5 is preferably smaller than the weight of the super absorbent polymer 12 in the polymer arranged area 13 in the above polymer sheet 4, and is 0 to 30 g/m², and preferably 0 to 15 g/m². As the ratio of the weight of the super absorbent polymer in the above fiber absorber 5 and the weight of the super absorbent polymer 12 in the polymer arranged area 13 in the above polymer sheet 4, the ratio of the polymer weight of the fiber absorber 5 to the polymer weight of the polymer sheet 4 is 0 to 10%, and preferably 0 to 5%.

In addition, a synthetic fiber can be mixed in the above fiber absorber 5. As the above synthetic fiber, for example, a polyolefin-based fiber such as polyethylene or polypropylene, a polyester-based fiber such as polyethylene terephthalate or polybutylene terephthalate, a polyamide-based fiber such as nylon, and copolymers thereof and the like can be used, or a fiber obtained by mixing two of these can be also used. In addition, a core sheath fiber having a fiber with a high melting point as a core and a fiber with a low melting point as a sheath, a side-by-side fiber, and a conjugated fiber such as a segmented fiber can be also used. When the above synthetic fiber is a hydrophobic fiber, it is desired that synthetic fiber be subjected to surface treatment with a hydrophilizing agent to provide an affinity for a body fluid, and then used.

As shown in FIGS. 5(A) and (B), the planar shape of the above fiber absorber 5 is an almost square in which the longitudinal direction of a pad is longer in an example shown; however, the fiber absorber 5 can be formed in various forms such as an ellipse and oval. The length in the longitudinal direction of the napkin is 10 to 200 mm and preferably 30 to 70 mm, and the length in the width direction of the napkin is 10 to 60 mm and preferably 30 to 50 mm.

As the above fiber absorber 5, a fiber stacked absorber obtained by supplying, for example, a finely pulverized pulp fiber and the super absorbent polymer 12, which is mixed as needed, to a fiber stacking rotary drum having an absorber forming concave portion formed on the outer periphery thereof to stack the fiber is used, or an airlaid absorber obtained by spreading and mixing, for example, the above pulp fiber and the super absorbent polymer, which is mixed as needed, by an air-lay method and simultaneously aggregating and forming the fiber, and also reducing the thickness by pressure is preferably used.

As shown in FIGS. 5(A) and (B), the above fiber absorber 5 can be surrounded by an enveloping sheet 9 having e.g. crepe paper or a nonwoven fabric to prevent the falling of the fiber and super absorbent polymer. In this case, as a result, the enveloping sheet 9 exists between the permeable front-surface sheet 3 and the fiber absorber 5, and a body fluid quickly spreads by the above enveloping sheet 9 having excellent absorption properties, and also a return of the body fluid is prevented.

In the sanitary napkin 1 having the above configuration, an absorbing structure to retain a body fluid is configured from the polymer sheet 4, and the fiber absorber 5 disposed adjacent to the surface on the skin side of an area corresponding to a body fluid discharge region H of a wearer in this polymer sheet 4. Because the above fiber absorber 5 is laminated only in the area corresponding to a body fluid discharge region H of a wearer, a reduction in thickness of the sanitary napkin 1 by using the polymer sheet 4 can be certainly attempted.

In addition, in the sanitary napkin 1, the super absorbent polymer 12 in the polymer sheet 4 is not arranged in an area which overlaps with the fiber absorber 5 and is arranged in the other area, and thus the water absorption rate is not reduced even when water is repeatedly absorbed, and leakage of a body fluid can be prevented. To be more specific, as shown in FIG. 6, a body fluid discharged from a body fluid discharge region H is absorbed by the fiber absorber 5 disposed in an area corresponding to the body fluid discharge region H of a wearer, and then penetrates into the non-polymer area 14 in the polymer sheet 4 adjacent to the lower layer side thereof. The body fluid having penetrated into the polymer sheet 4 passes through gaps between the upper layer sheet 10 and lower layer sheet 11, spreads in the surface direction, also spreads into the upper layer sheet 10 and lower layer sheet 11 in the surface direction by the capillary action of fiber, and is sequentially absorbed and retained by the super absorbent polymer 12 in the polymer sheet 4 during the process of spreading in the surface direction. That is, when a body fluid moves from the fiber absorber 5 to the polymer sheet 4, because the body fluid does not pass through an area in which the super absorbent polymer 12 is disposed in the direction of the thickness of the sanitary napkin 1, a problem of impermeability of the body fluid due to gel blocking does not occur, a significant reduction in the water absorption rate is not caused even when water is repeatedly absorbed, and leakage of the body fluid can be prevented.

In the above polymer sheet 4, the super absorbent polymer is not arranged in an area which overlaps with the fiber absorber 5. Accordingly, in the area which overlaps with the fiber absorber 5 in the above polymer sheet 4, the super absorbent polymer is not swollen and lifted toward the skin when the polymer sheet 4 absorbs a fluid, and an almost equal height can be maintained before and after absorbing the fluid. Therefore, a worsening of a wearing feeling due to the fiber absorber 5 being lifted toward the skin and biting into the body more than necessary can be prevented.

In addition, even when a large amount of body fluid is discharged at once, the above fiber absorber 5 plays a role as a temporal storage tank for the body fluid, and a role as a spreading layer which spreads the body fluid in the surface direction to an extent and then moves the body fluid to the polymer sheet 4. The body fluid can smoothly move to the polymer sheet 4, and absorption properties for the body fluid can be improved.

As described above, when the above fiber absorber 5 is configured from only pulp fiber, a body fluid temporarily absorbed by pulp fiber can quickly move to the polymer sheet 4. On the other hand, when the fiber absorber 5 is configured from pulp fiber and the super absorbent polymer 12, the fiber absorber 5 has a certain level of absorption ability. However, in order to prevent gel blocking in the fiber absorber 5 and promote the transfer of the body fluid to the polymer sheet 4, it is preferred that the super absorbent polymer 12 be included in the fiber absorber 5 in a fixed amount or less as described above.

To be further more specific about the above polymer sheet 4 and fiber absorber 5, in a state in which the above fiber absorber 5 is arranged on the surface on the skin side of the polymer sheet 4, it is preferred that the surface on the skin side of the above fiber absorber 5 be located at a height almost equal to that of the surface on the skin side of the polymer arranged area 13 in the above polymer sheet 4, or located closer to the skin than the surface on the skin side of the above polymer arranged area 13. When the surface on the skin side of the fiber absorber 5 and the surface on the skin side of the polymer arranged area 13 in the polymer sheet 4 are located at almost the same height, a reduction in thickness of the sanitary napkin 1 can be still further attempted. At this time, as the above fiber absorber 5, a thin airlaid absorber is preferably used. On the other hand, when the height of the surface on the skin side of the above fiber absorber 5 is higher toward the skin than the height of the surface on the skin side of the above polymer arranged area 13, the above fiber absorber 5 functions as a middle-height portion, and adhesion to a body fluid discharge region H of a wearer can be improved. A difference in height between the surface on the skin side of the above fiber absorber 5 and the surface on the skin side of the polymer arranged area 13 is preferably about 0 to 5 mm.

As shown in FIG. 7 and FIG. 8, one or more openings 15 penetrating through the front and back surfaces can be formed in the above fiber absorber 5. By forming the above openings 15, a body fluid can more quickly move from the fiber absorber 5 to polymer sheet 4 through these openings 15. The above openings 15 are openings penetrating through the front and back surfaces of the fiber absorber 5 in a linear manner, which openings are formed by e.g. pricks with a pin or a mold during stacking fiber. In an example shown, the above openings 15 are formed at two spots separated in the longitudinal direction of the napkin in the central part of the fiber absorber 5 in the width direction of the napkin. However, the openings can be formed at one or three spots or more, and a plurality of openings separated in the width direction of the napkin can be formed. In addition, the planar shape of the above opening 15 is circle in an example shown; however, the shapes of an ellipse and a slit are optionally used.

As shown in FIG. 9 and FIG. 10, concave portions 16 and 17 depressed to the polymer sheet 4 can be formed on the surface on the skin side in the fiber absorber 5. By forming the above concave portions 16 and 17, a body fluid having entered the concave portions 16 and 17 can quickly move to the polymer sheet 4. In an example shown in FIG. 9, the fiber absorber 5 is disposed on the surface on the skin side of the polymer sheet 4, a concave portion 16 is formed by pressing the above fiber absorber 5 and polymer sheet 4 in an integrated manner from the skin side of the above fiber absorber 5, and then the permeable front-surface sheet 3 and second sheet 6 are disposed on the skin side. In addition, in an example shown in FIG. 10, the fiber absorber 5 is disposed on the surface on the skin side of the polymer sheet 4, and also the second sheet 6 and permeable front-surface sheet 3 are disposed on the surface on the skin side thereof, and a concave portion 17 is formed by pressing the above permeable front-surface sheet 3, second sheet 6, fiber absorber 5 and polymer sheet 4 in an integrated manner by pressing from the skin side of the above permeable front-surface sheet 3. As the planar shape, the above concave portions 16 and 17 can be formed in the form of a groove in the central part in the width direction of the fiber absorber 5, which groove spreads over a whole length in the longitudinal direction of the napkin, and a plurality of patterns such as the form of a circle can be arranged at one or more spots.

In the above polymer sheet 4, to seal the super absorbent polymer 12 in a predetermined area between the upper layer sheet 10 and lower layer sheet 11, joint portions joining the above upper layer sheet 10 and lower layer sheet 11 are provided in a predetermined form. As shown in FIG. 3 and FIG. 4, as a first embodiment of the above joint portions the polymer arranged area 13 is divided into a plurality of defined areas 20, 20 . . . by the joint portions 18 and 19 joining the upper layer sheet 10 and lower layer sheet 11, and also the super absorbent polymer 12 is arranged in the above defined areas 20. In this form, the polymer arranged area 13 is divided into a plurality of defined areas 20 . . . . Accordingly, even when the super absorbent polymer 12 sealed in each defined area 20 is swollen when absorbing water and each defined area 20 is lifted, the surrounding joint portions 18 and 19 are not lifted. Because of this, a body fluid easily spreads using these joint portions 18 and 19 as channels even when water is repeatedly absorbed.

To be further more specific about the planar pattern of the joint portions 18 and 19 shown in FIG. 3 and FIG. 4, the top and bottom, left and right positions of the above defined area 20 in a planar view are surrounded by the first joint portions 18 joining the upper layer sheet 10 to the lower layer sheet 11, and also the intermediate position of an oblique line joining the first joint portions 18, 18 is surrounded by the second joint portions 19 joining the upper layer sheet 10 to the lower layer sheet 11. The joint portions are aligned in the form of a regular grid along the longitudinal direction and width direction of the sanitary napkin 1.

To be further more specific, as shown in FIG. 11, in the above polymer sheet 4, the upper layer sheet 10 and lower layer sheet 11 are joined by the first joint portions 18 provided in the arrangement of the form of houndstooth, and also joined by the second joint portions 19 provided in the intermediate position of an oblique line joining 4 first joint portions 18, 18 . . . existing in the top and bottom, left and right positions. The above arrangement in the form of houndstooth is an arrangement in which lines or rows next to each other at the same pitch are shifted by a half pitch in every other line or every other row, and arranged to align vertically and horizontally in every other line or every other row. In addition, in the description, the top and bottom positions are positions in a direction corresponding to the longitudinal direction (front-back direction) of the sanitary napkin 1, and the left and right positions are positions in a direction corresponding to the width direction of the sanitary napkin 1.

The super absorbent polymer 12 is arranged in the inner part of a plurality of defined areas 20, which are surrounded by the above first joint portion 18 and second joint portion 19 in the above polymer arranged area 13 and also aligned in the form of a regular grid along the longitudinal direction and width directions of the napkin.

As shown in FIG. 11, the above first joint portions 18 arranged on the top and bottom ends of the above defined area 20 are preferably formed in the form of a long groove in the horizontal direction (the width direction of the napkin), and the first joint portions 18 arranged on the left and right ends of the defined area 20 are preferably formed in the form of a long groove in the vertical direction (the longitudinal direction of the napkin). Because of this, the first joint portion 18 is formed in the form of a long groove between the defined areas 20, 20 next to each other in the direction of a tangent to which the areas each connect, and a channel through which a body fluid flows is easily formed between defined areas 20, 20 next to each other. It should be noted that the above first joint portion 18 is preferably formed in the form of a continuous groove, but can be also formed in the form of intermittent dots.

In addition, the above second joint portion 19 is arranged apart from the above first joint portion 18, and also is preferably formed in the form of a plurality of intermittent dots in a direction joining first joint portions 18, 18 next to each other. The above second joint portion 19 can be formed in the form of intermittent dots, which have a weaker joining strength than the first joint portion 18, to preferentially come off when the super absorbent polymer 12 is swollen by absorbing a fluid, or can be formed in the form of a continuous groove.

The above joint portions 18 and 19 are not continuously formed on the surroundings of the above defined area 20, and have a portion which is not joined and are intermittently formed. Therefore, a body fluid having flown into a defined area 20 easily spreads into the adjacent defined area 20 through the portion which is not joined.

The above joint portions 18 and 19 can be also provided to the above non-polymer area 14 in the same pattern, or can be also provided in a pattern different from that of the polymer arranged area 13 as described in a later paragraph.

As shown in FIGS. 12(A) to (D), the planar pattern of the above joint portion can be formed in various forms. In FIG. 12(A), the sheets are joined by the joint portions 23, 23 . . . provided on 4 positions in oblique directions of a defined area 20, and also predetermined positions in the defined area 20 are joined by the joint portions 24, 24 . . . In addition, in FIGS. 12(B) to (D), the sheets are joined by the joint portions 25 continuously or intermittently provided in the longitudinal direction of the napkin, and the defined areas 20 are intermittently or continuously formed in the longitudinal direction of the napkin in an area in which both sides in the width direction of the napkin are sandwiched in between the above joint portions 25.

Next, as a second embodiment of the above joint portion, as shown in FIG. 13, the above polymer arranged area 13 is not divided by joint portions joining the upper layer sheet 10 and lower layer sheet 11, and the super absorbent polymer 12 is arranged on a whole surface. That is, the upper layer sheet 10 and lower layer sheet 11 are joined only by an outer joint portion 21 provided to surround the surroundings of the polymer arranged area 13, and an inner joint portion 22 provided along the boundary of the polymer arranged area 13 and non-polymer area 14, and also the above super absorbent polymer 12 is arranged on an almost whole surface in an area surrounded by the above outer joint portion 21 and inner joint portion 22. In this form, the super absorbent polymer 12 is sealed in a relatively wide area, and thus the super absorbent polymer 12 has a high flowability in the polymer arranged area 13 even when being swollen by absorbing water, and a reduction in absorption performance due to gel blocking does not easily occur.

The joint portion of the above upper layer sheet 10 and lower layer sheet 11 can be joined by a joining method with heat welding or ultrasonic welding by pressing from the outer side of the upper layer sheet 10, or a joining method with a hot melt adhesive. In adhesion with a hot melt adhesive, it is preferred that the adhesive be applied in the form of a streak or a sheet by any applying method such as slot, summit or spiral, and a super absorbent polymer 12 in the form of granule be scattered thereon.

The above joint portion can be provided to both the polymer arranged area 13 and non-polymer area 14 in the same pattern (that is, a whole surface of the polymer sheet 4); however, as shown in FIG. 14, in order to promote the spread of a body fluid into the surrounding polymer arranged area 13, the joint portion in the non-polymer area 14 is preferably provided in a pattern different from that of the above polymer arranged area 13. In FIG. 14(A), the joint portions 26 are provided in a radial fashion from the central part of the non-polymer area 14, and in FIG. 14(B), the joint portions 27 are provided in the form of a streak along the non-polymer area 14 in the longitudinal direction of the napkin at intervals in the width direction of the napkin. Because of this, a body fluid having penetrated into the central part of the non-polymer area 14 easily spreads along each joint portion 26, 27 toward the surrounding polymer arranged area 13.

REFERENCE SIGN LIST

1: Sanitary napkin, 2: Impermeable back-surface sheet, 3: Permeable front-surface sheet, 4: Polymer sheet, 5: Fiber absorber, 6: Second sheet, 7: Side nonwoven fabric, 8: String-like elastic stretch member, 9: Enveloping sheet, 10: Upper layer sheet, 11: Lower layer sheet, 12: Super absorbent polymer, 13: Polymer arranged area, 14: Non-polymer area, 15: Opening, 16, 17: Concave portion, 18, 19: Joint portion, 20: Defined area, 21: Outer joint portion, 22: Inner joint portion.

The invention claimed is:

1. An absorbent article, comprising a polymer sheet in which a super absorbent polymer exists between an upper layer sheet arranged on a skin side and a lower layer sheet arranged on a non-skin side, the polymer sheet having an area corresponding to a body fluid discharge region of a wearer, the absorbent article being characterized in that a fiber absorber comprising pulp fiber is disposed adjacent to a surface on a skin side of said area of the polymer sheet, and the polymer sheet comprises a polymer arranged area in which the super absorbent polymer exists between the upper layer sheet and the lower layer sheet in an area which does not overlap with the fiber absorber, and a non-polymer area in which the super absorbent polymer does not exist between the upper layer sheet and the lower layer sheet in an area which overlaps with the fiber absorber, wherein the non-polymer area has a depressed area in which a surface on a skin side is depressed compared to the polymer arranged area surrounding the non-polymer area due to non-existence of the super absorbent polymer, and the fiber absorber is arranged to fit the depressed area of the non-polymer area.

2. The absorbent article according to claim 1, wherein the fiber absorber comprises only pulp fiber or comprises pulp fiber and a super absorbent polymer.

3. The absorbent article according to claim 1, wherein a difference in height between a surface on a skin side of the fiber absorber and a surface on a skin side of the polymer arranged area of the polymer sheet is 0 to 5 mm.

4. The absorbent article according to claim 1, wherein one or more openings penetrating from front to back are formed in the fiber absorber.

5. The absorbent article according to claim 1, wherein a concave portion depressed to the polymer sheet is formed on a surface on a skin side of the fiber absorber.

6. The absorbent article according to claim 1, wherein an area in which the super absorbent polymer is arranged in the polymer sheet is divided into a plurality of defined areas by joint portions joining the upper layer sheet and lower layer sheet and also the super absorbent polymer is arranged in the defined areas, or an area in which the super absorbent polymer is arranged is not divided by joint portions joining the upper layer sheet and lower layer sheet and the super absorbent polymer is arranged on a whole surface.

* * * * *